US011071632B2

(12) United States Patent
Oh et al.

(10) Patent No.: US 11,071,632 B2
(45) Date of Patent: Jul. 27, 2021

(54) INTERVERTEBRAL IMPLANT DEVICE

(71) Applicants: Young Hoon Oh, Montville, NJ (US); Rachel Oh, Montville, NJ (US)

(72) Inventors: Young Hoon Oh, Montville, NJ (US); Rachel Oh, Montville, NJ (US)

( * ) Notice: Subject to any disclaimer, the term of this patent is extended or adjusted under 35 U.S.C. 154(b) by 0 days.

(21) Appl. No.: 16/840,381

(22) Filed: Apr. 4, 2020

(65) Prior Publication Data
US 2020/0237524 A1    Jul. 30, 2020

(51) Int. Cl.
*A61F 2/44* (2006.01)

(52) U.S. Cl.
CPC ...... *A61F 2/4425* (2013.01); *A61F 2002/443* (2013.01); *A61F 2220/0016* (2013.01); *A61F 2220/0025* (2013.01)

(58) Field of Classification Search
CPC ............ A61F 2/4425; A61F 2220/0025; A61F 2220/0016; A61F 2002/443; A61F 2002/30329; A61F 2002/30841; A61F 2/4611; A61F 2002/30014; A61F 2002/30069; A61F 2002/30281; A61F 2002/30563; A61F 2002/30576; A61F 2002/30578; A61F 2/442
See application file for complete search history.

(56) References Cited

U.S. PATENT DOCUMENTS

| | | | |
|---|---|---|---|
| 10,154,910 B2 | 12/2018 | Reichen et al. | |
| 10,258,482 B1 | 4/2019 | Yu | |
| 10,357,376 B2 | 7/2019 | de Villiers et al. | |
| 10,413,420 B2 | 9/2019 | de Villiers et al. | |
| 10,492,919 B2 | 12/2019 | Rashbaum et al. | |
| 10,517,733 B2 | 12/2019 | de Villiers et al. | |
| 10,517,738 B2 | 12/2019 | de Villiers et al. | |
| 10,548,739 B2 | 2/2020 | de Villiers et al. | |
| 2004/0267369 A1* | 12/2004 | Lyons | A61F 2/442 623/17.16 |
| 2009/0088850 A1* | 4/2009 | Froehlich | A61F 2/4425 623/17.16 |

* cited by examiner

*Primary Examiner* — Jerrah Edwards
*Assistant Examiner* — Jared Klar Rovira
(74) *Attorney, Agent, or Firm* — Rahman LLC

(57) ABSTRACT

An intervertebral implant device includes a first plate having a first fixation component; and a first set of outwardly extending projecting members. The device also includes a second plate having a second fixation component; and a second set of outwardly extending projecting members that compliment an alignment with the first set of outwardly extending projecting members. The device also includes a core member that extends through the first plate and the second plate. The core member limits movement of the first plate away from the second plate; and a connecting member that connects to the core member.

20 Claims, 12 Drawing Sheets

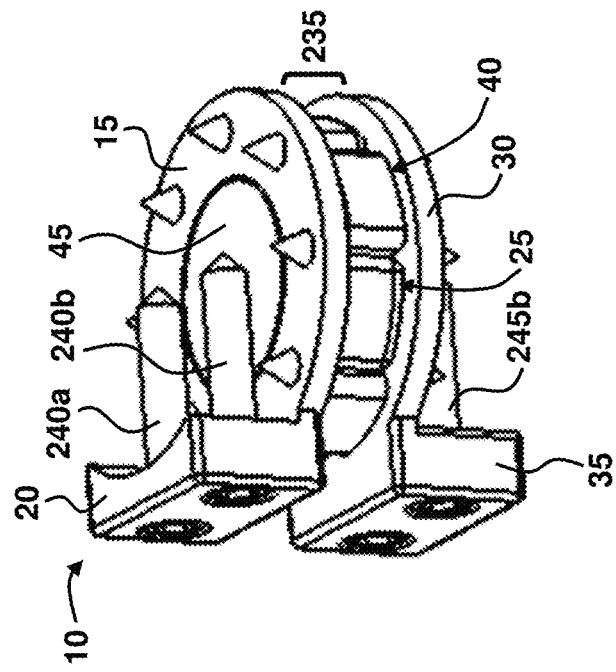
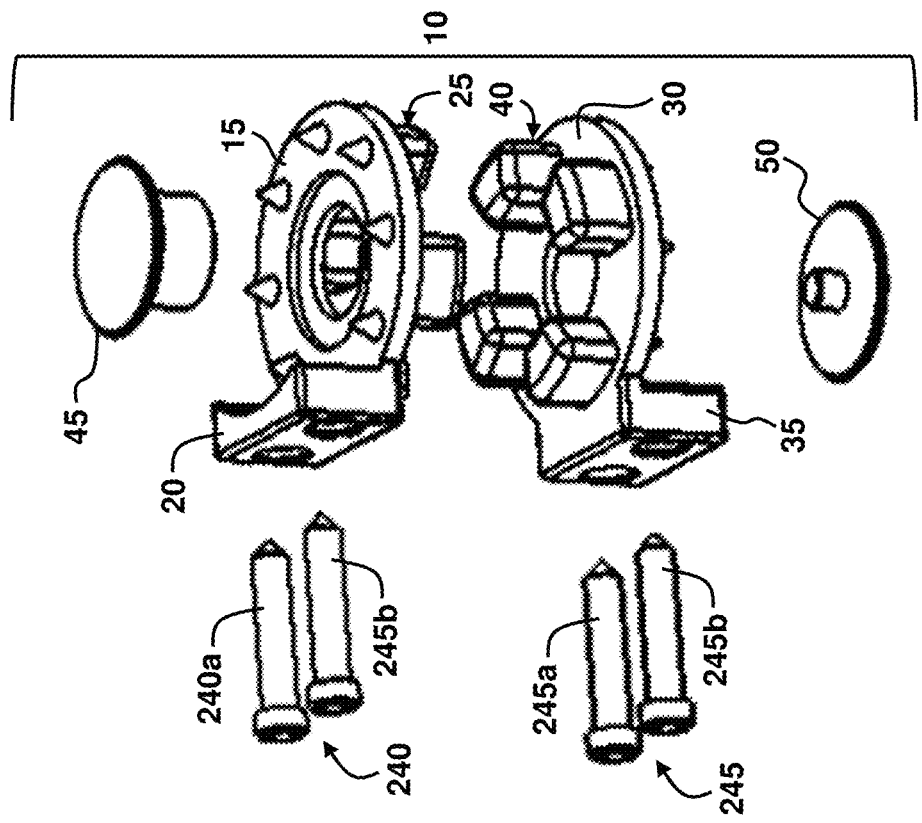

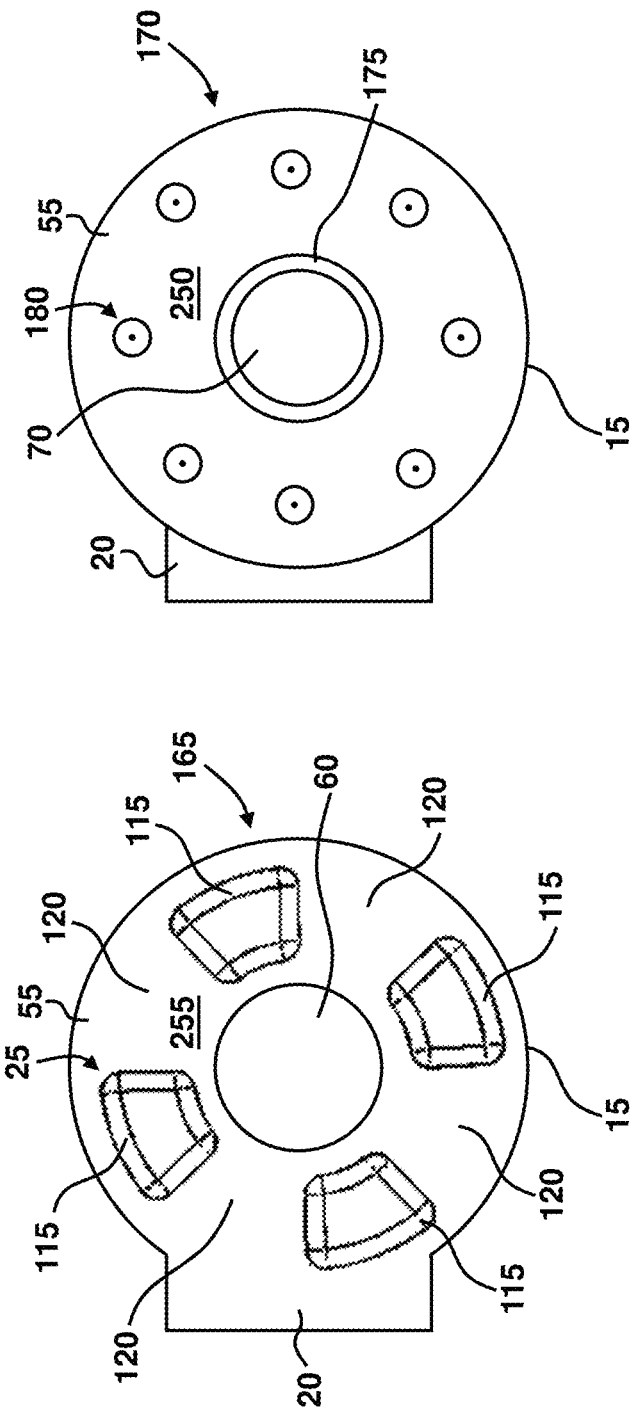

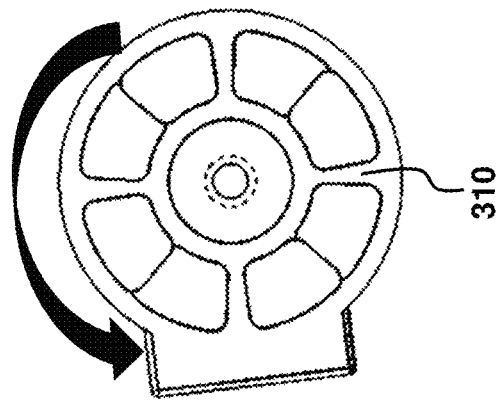
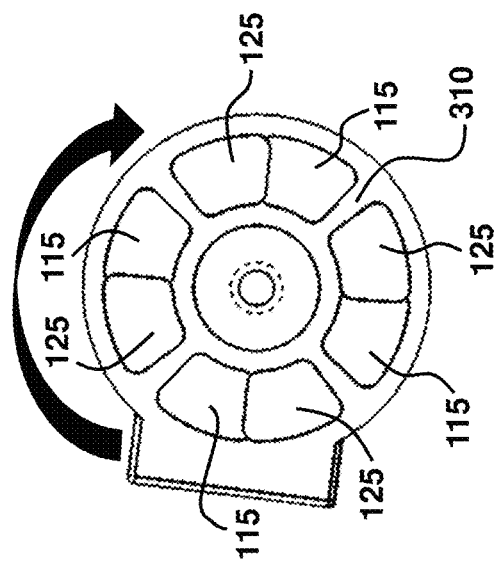
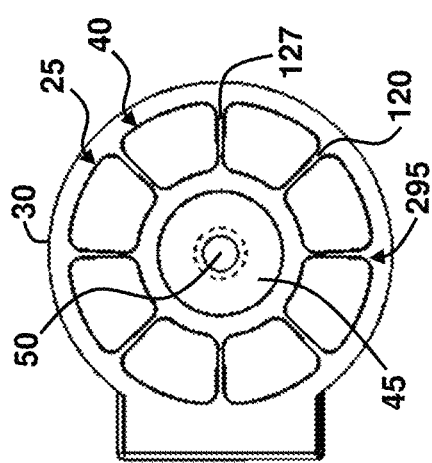

INTERVERTEBRAL IMPLANT DEVICE

BACKGROUND

Technical Field

The embodiments herein generally relate to medical devices, and more particularly to intervertebral implant devices.

Description of the Related Art

Intervertebral discs are soft tissue structures that generally provide a cushion between adjacent vertebrae in the spine. However, due to injury or biological degeneration, these intervertebral discs may no longer provide sufficient protection for the vertebrae, which can cause significant back pain. In order to alleviate chronic back pain caused by injured or degenerative intervertebral discs, surgery is often necessary. One example type of surgical technique is to implant an artificial disc in the intervertebral space between each of two vertebrae to replace the damaged intervertebral discs. Generally, artificial implant discs used to substitute an intervertebral disc have a center of rotation (COR) point that is near the center of the intervertebral disc space. Moreover, the center of rotation of the cervical disc is near the center of the intervertebral body. However, for the lumbar disc region, the center of rotation point is near the outer rim of the intervertebral disc space. This mismatch of the center of rotation point may result in constrained or inferior vertebral movement, damaged artificial disc components, and continued back pain, which may eventually necessitate further surgeries. This can cause an increased risk of infection to the patient, damage to other healthy vertebrae, an increased requirement for hospitalization and rehabilitation, and an overall lower quality of life.

SUMMARY

In view of the foregoing, an embodiment herein provides an intervertebral implant device comprising a first plate comprising a first fixation component; and a first set of outwardly extending projecting members. The device also includes a second plate comprising a second fixation component; and a second set of outwardly extending projecting members that compliment an alignment with the first set of outwardly extending projecting members. The device also includes a core member that extends through the first plate and the second plate, wherein the core member limits movement of the first plate away from the second plate; and a connecting member that connects to the core member.

The first plate comprises a first body portion comprising a first hole configured therethrough, wherein the first hole accommodates the core member, wherein the second plate comprises a second body portion comprising a second hole configured therethrough, wherein the second hole aligns with the first hole, and wherein the second hole accommodates the core member and the connecting member. The first fixation component extends from an outer edge of the first body portion of the first plate, wherein the first fixation component comprises a first at least one hole configured therethrough, and wherein a first axis through the first hole of the first body portion and a second axis through the first at least one hole of the first fixation component are perpendicular to each other.

The second fixation component extends from an outer edge of the second body portion of the second plate, wherein the second fixation component comprises a second at least one hole configured therethrough, and wherein a third axis through the second hole of the second body portion and a fourth axis through the second at least one hole of the second fixation component are perpendicular to each other. The first axis and the third axis are co-linear. The second axis and the fourth axis are parallel. The first set of outwardly extending projecting members comprise a first plurality of annulus sector members spaced apart from each other by a first plurality of spaces, and wherein the first plurality of annulus sector members are positioned in a substantially annular arrangement on the first plate. The second set of outwardly extending projecting members comprise a second plurality of annulus sector members spaced apart from each other by a second plurality of spaces, and wherein the second plurality of annulus sector members are positioned in a substantially annular arrangement on the second plate.

The first plurality of annulus sector members fit into the second plurality of spaces and adjacent to the second plurality of annulus sector members, and wherein the second plurality of annulus sector members fit into the first plurality of spaces and adjacent to the first plurality of annulus sector members. The core member comprises a first head portion comprising a first outer surface; a first neck portion extending from the first head portion; and a third hole in the first neck portion, wherein the connecting member comprises a second head portion comprising a second outer surface; and a second neck portion extending from the second head portion, wherein the first head portion extends through the first hole of the first body portion of the first plate and in the second hole of the second body portion of the second plate, and wherein the second neck portion engages the third hole of the core member. The first outer surface of the first head portion and the second outer surface of the second head portion face in opposite directions from each other.

The first body portion of the first plate comprises a first side and an oppositely facing second side, wherein the first side comprises the first set of outwardly extending projecting members, wherein the second side comprises a groove and a plurality of outwardly extending spikes, and wherein the groove accommodates the first head portion of the core member. The second body portion of the second plate comprises a first side and an oppositely facing second side, wherein the first side comprises the second set of outwardly extending projecting members, wherein the second side comprises a groove and a plurality of outwardly extending spikes, and wherein the groove accommodates the second head portion of the connecting member. The first fixation component comprises a first bar containing the first at least one hole, wherein the first bar comprises a first side and an oppositely positioned second side, wherein the second side is adjacent to the first plate, and wherein the second side is substantially arcuately shaped. The second fixation component comprises a second bar containing the second at least one hole, wherein the second bar comprises a first side and an oppositely positioned second side, wherein the second side is adjacent to the second plate, and wherein the second side is substantially arcuately shaped.

A spacing between the first plate and the second plate is defined by a height of any of the first set of outwardly extending projecting members and the second set of outwardly extending projecting members. The device may comprise at least one first fixation member that engages the first at least one hole of the first fixation component; and at least one second fixation member that engages the second at least one hole of the second fixation component. The first body portion, the second body portion, the first fixation component, and the second fixation component are formed of a first material that is substantially rigid, and wherein the first set of outwardly extending projecting members and the second set of outwardly extending projecting members are formed of a second material that is substantially flexible.

Another embodiment provides an intervertebral implant device comprising a first plate comprising a first surface; and a second surface opposed to the first surface, wherein the second surface comprises a first set of projecting members outwardly extending from the second surface. The device also includes a second plate comprising a third surface; and a fourth surface opposed to the third surface, wherein the fourth surface comprises a second set of projecting members outwardly extending from the fourth surface, wherein the second set of projecting members are configured to complimentarily align adjacent with the first set of projecting members. The device also includes a core member that extends through the first plate and the second plate, wherein the core member limits movement of the first plate away from the second plate; a connecting member that connects to the core member; at least one first fixation member configured to engage the first plate; and at least one second fixation member configured to engage the second plate.

Another embodiment provides an intervertebral implant device for insertion into an intervertebral space between a first vertebra and a second vertebra, the device comprising a first plate comprising a first surface that contacts a first end plate of the first vertebra; and a second surface opposed to the first surface, wherein the second surface comprises a first set of outwardly extending projecting members that are flexible. The device also includes a second plate comprising a third surface that contacts a second end plate of the second vertebra; and a fourth surface opposed to the third surface, wherein the fourth surface faces the second surface, wherein the fourth surface comprises a second set of outwardly extending projecting members that are flexible, and wherein the second set of projecting members complimentarily align between the first set of projecting members creating an annulus between the first plate and the second plate. The device also includes a core member that extends through the first plate and the second plate, wherein the core member extends through the annulus and limits an extension of the intervertebral space; a connecting member that connects to the core member and retains operative connectivity of the first plate with the second plate; a first fixation component attached to the first plate, wherein the first fixation component accommodates at least one first fixation member that operatively connects the first plate to the first vertebra; and a second fixation component attached to the second plate, wherein the second fixation component accommodates at least one second fixation member that operatively connects the second plate to the second vertebra.

Another embodiment provides a method of inserting an intervertebral implant device into the intervertebral space between a first vertebra and a second vertebra. The method comprises providing an intervertebral implant device comprising a first plate with a compressible first set of outwardly extending projecting members, a second plate with a compressible second set of outwardly extending projecting members, a core member positioned in the first plate and the second plate, and a connecting member positioned in the second plate and attached to the core member; attaching the first plate to the first vertebra; attaching the second plate to the second vertebra; and aligning the compressible first set of outwardly extending projecting members with the compressible second set of outwardly extending projecting members to create an annulus such that the core member is positioned in the annulus, and such that the core member controls the extension of the intervertebral space.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 1A is a schematic diagram illustrating an exploded view of intervertebral implant device, according to an embodiment herein;

FIG. 1B is a schematic diagram illustrating an assembled view of the intervertebral implant device of FIGS. 1A and 1B, according to an embodiment herein;

FIG. 4A is a schematic diagram illustrating a plan view of a first side of the first plate of the intervertebral implant device of FIGS. 1A and 1B, according to an embodiment herein;

FIG. 4B is a schematic diagram illustrating a plan view of a second side of the first plate of the intervertebral implant device of FIGS. 1A and 1B, according to an embodiment herein;

FIG. 13A is a schematic diagram illustrating a plan view of part of the intervertebral implant device of FIGS. 1A and 1B in a neutral position, according to an embodiment herein;

FIG. 13B is a schematic diagram illustrating a plan view of part of the intervertebral implant device of FIGS. 1A and 1B in a state of clockwise rotation, according to an embodiment herein;

FIG. 13C is a schematic diagram illustrating a plan view of part of the intervertebral implant device of FIGS. 1A and 1B in a state of counterclockwise rotation, according to an embodiment herein.

DETAILED DESCRIPTION

Figure 3:
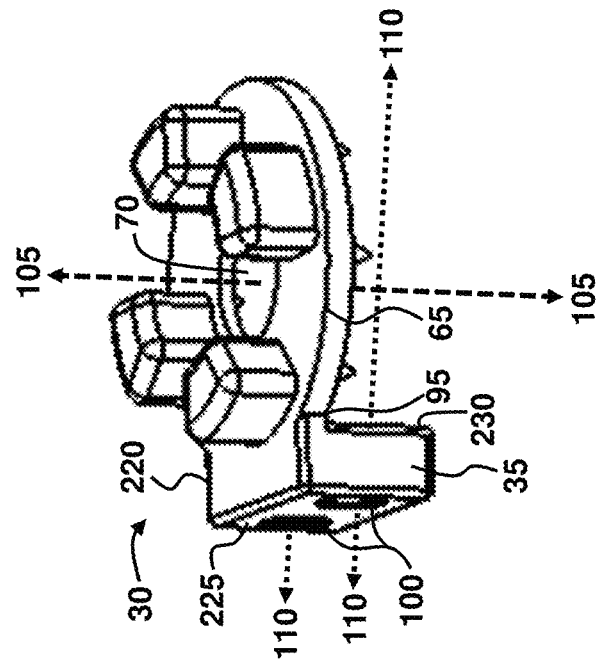
FIG. 3 is a schematic diagram illustrating a perspective view of the second plate of the intervertebral implant device of FIGS. 1A and 1B, according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, the COR of a cervical disc is near the center of the intervertebral body. However, for the lumbar disc region, the center of rotation point is near the outer rim of the intervertebral disc space. To create this motion, the embodiments herein provide an extension-limiting nucleus that may be flexible or rigid and restricts the extension, and the COR annulus projecting member is flexible, but is also sufficiently rigid to limit the compression. Furthermore, the embodiments herein provide an artificial intervertebral disc configured to meet these requirements and which rotates in an off-centered point along with moving in a controlled translation and axial rotation. Accordingly, the embodiments herein may be used to provide mobility to a person who needs to replace his/her intervertebral disc. Referring now to the drawings, and more particularly to FIGS. 1A through 14 where similar reference characters denote corresponding features consistently throughout the figures, there are shown example embodiments. In the drawings, the size and relative sizes of components, layers, and regions, etc. may be exaggerated for clarity.

FIGS. 1A and 1B are schematic diagrams illustrating an intervertebral implant device 10 comprising a first plate 15 comprising a first fixation component 20, and a first set of outwardly extending projecting members 25. In an example, the first plate 15 may be substantially circular in shape, although other shapes and configurations are possible. The first fixation component 20 may be a substantially block-like component attached to the edge of the first plate 15, according to an example. Moreover, the first fixation component 20 may extend above a height of the first plate 15, in an example. The first set of outwardly extending projecting members 25 may be substantially wedge-shaped components affixed or operatively connected to the first plate 15 and arranged in a substantially annular configuration.

The device 10 also includes a second plate 30 comprising a second fixation component 35, and a second set of outwardly extending projecting members 40. In an example, the second plate 30 may be substantially circular in shape, although other shapes and configurations are possible. The second fixation component 35 may be a substantially block-like component attached to the edge of the second plate 30, according to an example. Moreover, the second fixation component 35 may extend above a height of the second plate 30, in an example. The second set of outwardly extending projecting members 40 may be substantially wedge-shaped components affixed or operatively connected to the second plate 30 and arranged in a substantially annular configuration. Moreover, the second plate 30 may be configured to be substantially similar to the first plate 15. However, the arrangement of the second set of outwardly extending projecting members 40 on the second plate 30 is offset compared to the arrangement of the first set of outwardly extending projecting members 25 on the first plate 15. In this regard, the second set of outwardly extending projecting members 40 compliment an alignment with the first set of outwardly extending projecting members 25 when the first plate 15 is aligned and adjacent to the second plate 30 to allow the first set of outwardly extending projecting members 25 to interlock with the second set of outwardly extending projecting members 40.

The device 10 also includes a core member 45 that extends through the first plate 15 and the second plate 30. In an example, the core member 45 limits the movement of the first plate 15 away from or in relation to the second plate 30. The core member 45 may be configured to be suitably sized and shaped to permit the first plate 15 and the second plate 30 to rotate thereon. The device 10 also includes a connecting member 50 that connects to the core member 45. The connecting member 50 may be configured to be suitably sized and shaped to permit the second plate 30 to rotate thereon. The core member 45 and connecting member 50 may be configured in a female/male configuration, respectively, or vice versa, to accommodate connection therebetween. However, other configurations are possible to facilitate connection between the core member 45 and the connecting member 50 including having intervening components.

As shown in FIG. 1B, a spacing 235 between the first plate 15 and the second plate 30 is defined by a height of any of the first set of outwardly extending projecting members 25 and the second set of outwardly extending projecting members 40. As such, the height of the first set of outwardly extending projecting members 25 and the second set of outwardly extending projecting members 40 are substantially the same such that when the device 10 is fully assembled and in a neutral position or configuration, the spacing 235 between the first plate 15 and the second plate 30 is substantially uniform around the entire annular configuration of the mated first set of outwardly extending projecting members 25 with the second set of outwardly extending projecting members 40. As shown in FIGS. 1A and 1B, the device 10 may comprise at least one first fixation member 240 that engages the first at least one hole 80 of the first fixation component 20, and at least one second fixation member 245 that engages the at least one hole 100 of the second fixation component 35. In some examples, the at least one first fixation member 240 may comprise a pair of first fixation members 240a, 240b, and the at least one second fixation member 245 may comprise a pair of second fixation members 245a, 245b.

According to an example, the first body portion 55, the second body portion 65, the first fixation component 20, and the second fixation component 35 are formed of a first material that is substantially rigid such as stainless steel, aluminum, biopolymer, etc., or a combination thereof. Furthermore, the first set of outwardly extending projecting members 25 and the second set of outwardly extending projecting members 40 are formed of a second material that is substantially flexible polymers, soft ceramics, or hydrogels, etc., or a combination thereof. Moreover, in an example, the core member 45 and the connecting member 50 may be formed of substantially flexible or elastic material such as polymers, soft ceramics, or hydrogels, etc., or a combination thereof. In another example, the core member 45 and the connecting member 50 may be formed of substantially rigid material.

Figure 2:
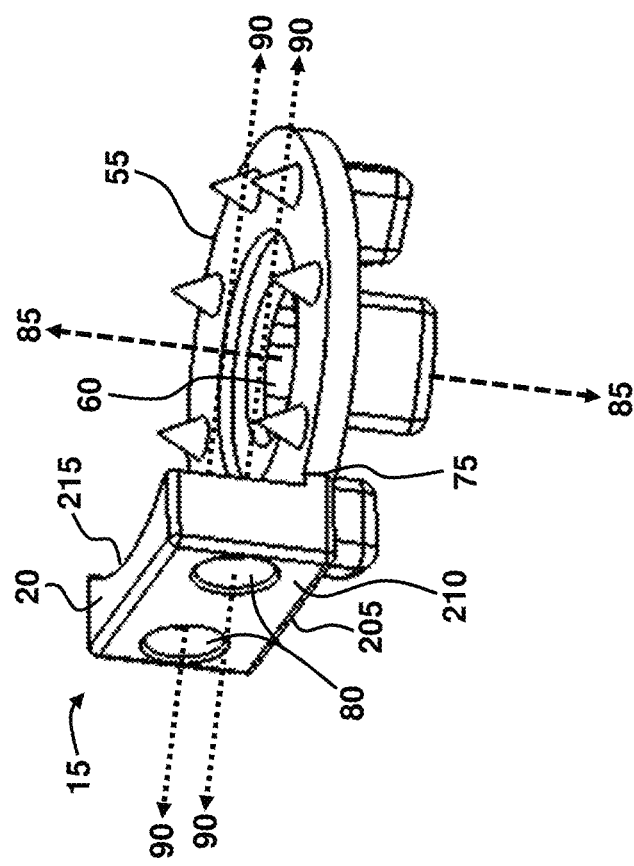
FIG. 2 is a schematic diagram illustrating a perspective view of the first plate of the intervertebral implant device of FIGS. 1A and 1B, according to an embodiment herein.

FIG. 2, with reference to FIGS. 1A and 1B, is a schematic diagram illustrating that the first plate 15 comprises a first body portion 55 comprising a first hole 60 configured therethrough, wherein the first hole 60 accommodates the core member 45. As shown in FIG. 2, the first fixation component 20 extends from an outer edge 75 of the first body portion 55 of the first plate 15. The first fixation component 20 comprises a first at least one hole 80 configured therethrough. In some examples, the number of the first at least one hole 80 matches the number of the at least one first fixation member 240. Moreover, in an example, a first axis 85 through the first hole 60 of the first body portion 55 and a second axis 90 through the first at least one hole 80 of the first fixation component 20 are perpendicular to each other. As shown in FIG. 2, the first fixation component 20 comprises a first bar 205 containing the first at least one hole 80. The first bar 205 comprises a first side 210 and an oppositely positioned second side 215. The second side 215 is adjacent to the first plate 15. Moreover, the second side 215 is substantially arcuately shaped to match the curved shape of the first body portion 55.

FIG. 3, with reference to FIGS. 1A through 2, is a schematic diagram illustrating that the second plate 30 comprises a second body portion 65 comprising a second hole 70 configured therethrough. The second hole 70 aligns with the first hole 60 when the device 10 is assembled. Furthermore, the second hole 70 accommodates the core member 45 and the connecting member 50. As shown in FIG. 3, the second fixation component 35 extends from an outer edge 95 of the second body portion 65 of the second plate 30. Additionally, the second fixation component 35 comprises a second at least one hole 100 configured therethrough. In some examples, the number of the second at least one hole 100 matches the number of the at least one second fixation member 245. Moreover, in an example, a third axis 105 through the second hole 70 of the second body portion 65 and a fourth axis 110 through the second at least one hole 100 of the second fixation component 35 are perpendicular to each other. As shown in FIG. 3, the second fixation component 35 comprises a second bar 220 containing the second at least one hole 100. The second bar 220 comprises a first side 225 and an oppositely positioned second side 230. The second side 230 is adjacent to the second plate 30. Moreover, the second side 230 is substantially arcuately shaped to match the curved shape of the second body portion 65. When the device 10 is assembled, the first axis 85 and the third axis 105 are co-linear, and the second axis 90 and the fourth axis 110 are parallel.

FIGS. 4A and 4B, with reference to FIGS. 1A through 3, are schematic diagrams illustrating that the first body portion 55 of the first plate 15 comprises a first side 165 and an oppositely facing second side 170. FIG. 4A illustrates the first side 165 containing a surface 255 of the first plate 15 and FIG. 4B illustrates the second side 170 containing a surface 250 of the first plate 15. The first side 165 comprises the first set of outwardly extending projecting members 25, which comprise a first plurality of annulus sector members 115 spaced apart from each other by a first plurality of spaces 120. There may be any suitably number of the first plurality of annulus sector members 115 constituting the first set of outwardly extending projecting members 25. In an example, there may be four of the first plurality of annulus sector members 115. In an example, the size of each of the spaces 120 is substantially the same as the size of each of the first plurality of annulus sector members 115 or the size of each of a second plurality of annulus sector members 125, which is further described below with reference to the second plate 30. The first plurality of annulus sector members 115 are positioned in a substantially annular arrangement on the first plate 15. In an example, the first plurality of annulus sector members 115 may be molded to the first side 165 of the first plate 15 or the first plurality of annulus sector members 115 may be attached to the first side 165 of the first plate 15 using any suitable type of fixation devices such as screws, pins, clips, or other attachment mechanisms, or a combination thereof. The second side 170 comprises a groove 175 and a plurality of outwardly extending spikes 180. According to an example, the spikes 180 may be substantially conically-shaped, although other shapes and configurations are possible so long as the spikes 180 can dig and set into vertebral bone. There may be any number of the plurality of outwardly extending spikes 180. Moreover, the spikes 180 may be arranged in any configuration on the second side 170 of the first plate 15. In an example, the plurality of outwardly extending spikes 180 may be arranged in a substantially circular arrangement. The spikes 180 may be molded to the second side 170 of the first plate 15 and may comprise the same rigid material as the first body portion 55 of the first plate 15. The groove 175 accommodates a first head portion 130 of the core member 45, as described below with reference to FIGS. 6A through 6D.

Figure 5B:
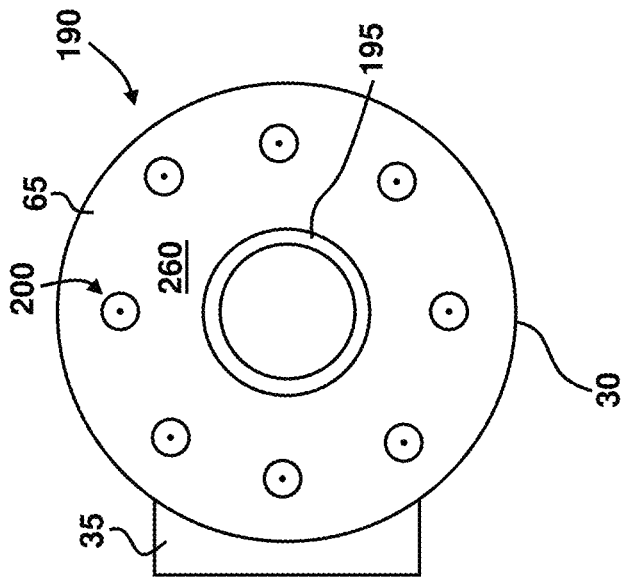
FIG. 5B is a schematic diagram illustrating a plan view of a second side of the second plate of the intervertebral implant device of FIGS. 1A and 1B, according to an embodiment herein.
Figure 5A:
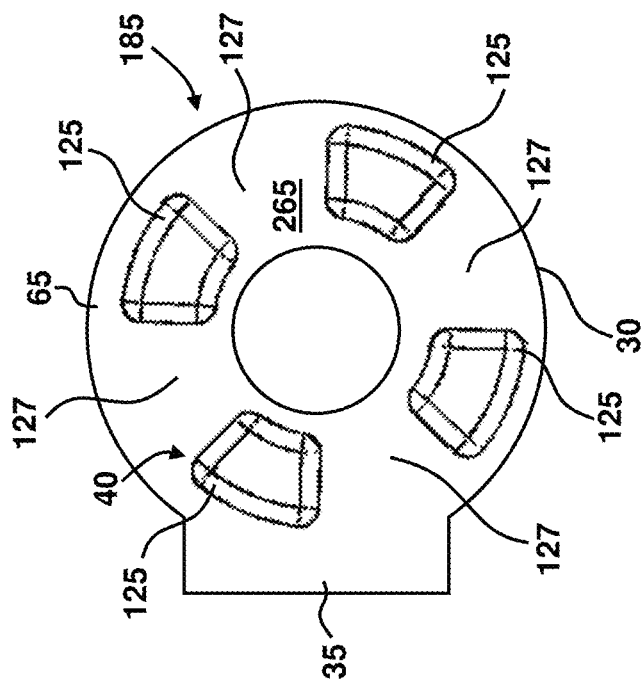
FIG. 5A is a schematic diagram illustrating a plan view of a first side of the second plate of the intervertebral implant device of FIGS. 1A and 1B, according to an embodiment herein.
Figure 6B:
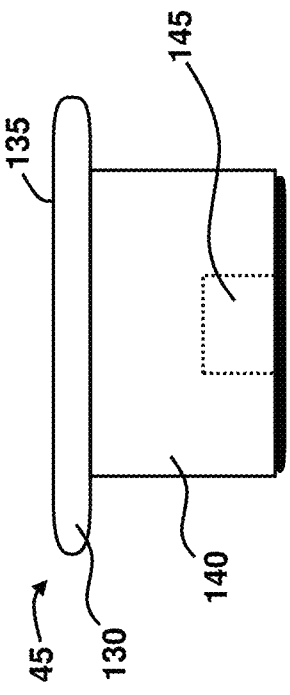
FIG. 6B is a schematic diagram illustrating a side view of the core member of FIG. 6A, according to an embodiment herein.
Figure 6D:
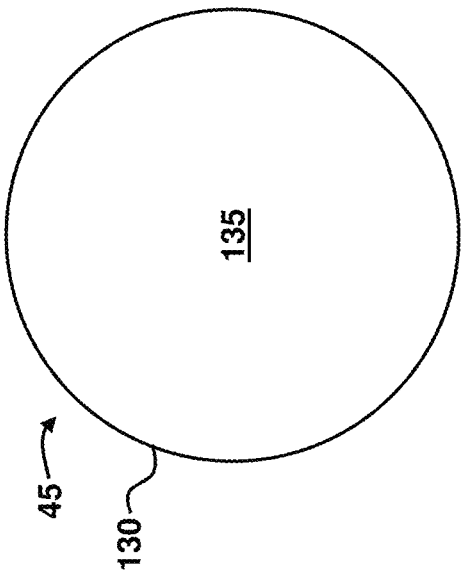
FIG. 6D is a schematic diagram illustrating a top plan view of the core member of FIG. 6A, according to an embodiment herein.
Figure 6A:
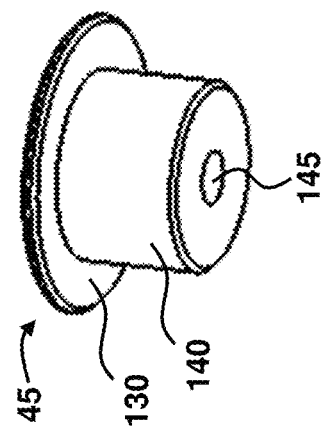
FIG. 6A is a schematic diagram illustrating a perspective view of the core member of the intervertebral implant device of FIGS. 1A and 1B, according to an embodiment herein.
Figure 6C:
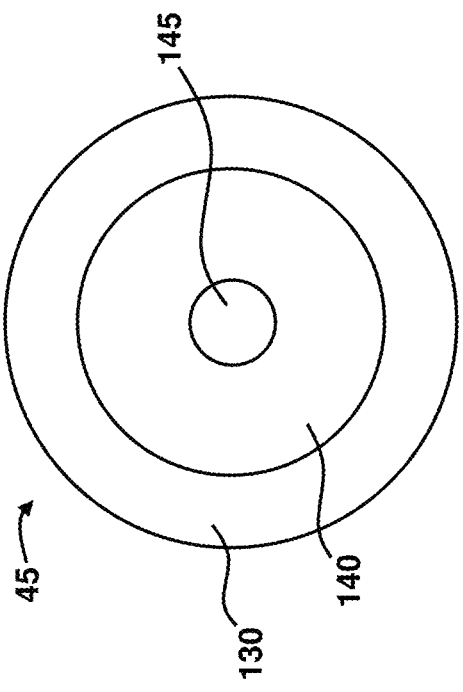
FIG. 6C is a schematic diagram illustrating a bottom plan view of the core member of FIG. 6A, according to an embodiment herein.
Figure 7B:
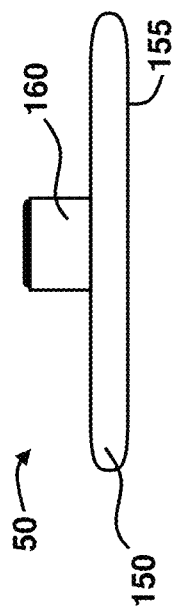
FIG. 7B is a schematic diagram illustrating a side view of the connecting member of FIG. 7A, according to an embodiment herein.
Figure 7D:
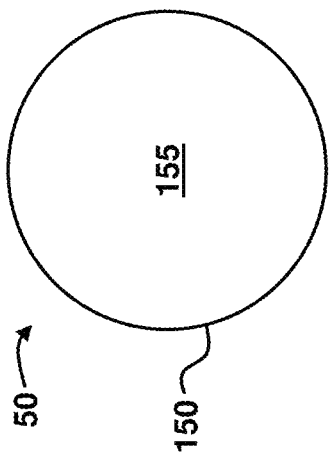
FIG. 7D is a schematic diagram illustrating a top plan view of the connecting member of FIG. 7A, according to an embodiment herein.
Figure 7A:
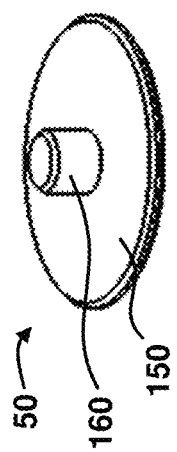
FIG. 7A is a schematic diagram illustrating a perspective view of the connecting member of the intervertebral implant device of FIGS. 1A and 1B, according to an embodiment herein.
Figure 7C:
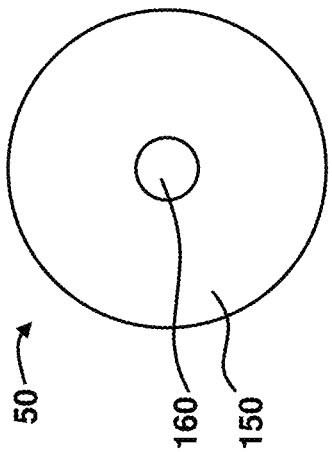
FIG. 7C is a schematic diagram illustrating a bottom plan view of the connecting member of FIG. 7A, according to an embodiment herein.

FIGS. 5A and 5B, with reference to FIGS. 1A through 4B, are schematic diagrams illustrating that the second body portion 65 of the second plate 30 comprises a first side 185 and an oppositely facing second side 190. FIG. 5A illustrates the first side 185 containing a surface 265 of the second plate 30 and FIG. 5B illustrates the second side 190 containing a surface 260 of the second plate 30. The first side 185 comprises the second set of outwardly extending projecting members 40, which comprise a second plurality of annulus sector members 125 spaced apart from each other by a second plurality of spaces 127. There may be any suitably number of the second plurality of annulus sector members 125 constituting the second set of outwardly extending projecting members 40. In an example, there may be four of the second plurality of annulus sector members 125. In an example, the size of each of the spaces 127 is substantially the same as the size of each of the second plurality of annulus sector members 125. In another example, the size of each of the first plurality of annulus sector members 115 is the same as the size of each of the second plurality of annulus sector members 125. Moreover, according to an example, the size of each of the spaces 127 of the second body portion 65 is the same as the size of each of the spaces 120 of the first body portion 55. The second plurality of annulus sector members 125 are positioned in a substantially annular arrangement on the second plate 30. In an example, the second plurality of annulus sector members 125 may be molded to the first side 185 of the second plate 30, or may be attached using any suitable type of fixation devices such as screws, pins, clips, or other attachment mechanisms, or a combination thereof. The second side 190 comprises a groove 195 and a plurality of outwardly extending spikes 200. According to an example, the spikes 200 may be substantially conically-shaped and similar to the spikes 180 of the first plate 15, although other shapes and configurations are possible so long as the spikes 200 can dig and set into vertebral bone. There may be any number of the plurality of outwardly extending spikes 200. Moreover, the spikes 200 may be arranged in any configuration on the second side 190 of the second plate 30. In an example, the plurality of outwardly extending spikes 200 may be arranged in a substantially circular arrangement. The spikes 200 may be molded to the second side 190 of the second plate 30 and may comprise the same rigid material as the second body portion 65 of the second plate 30. The groove 195 accommodates the second head portion 150 of the connecting member 50, as described below with reference to FIGS. 7A through 7D.

FIGS. 6A through 6D, with reference to FIGS. 1A through 5B, are schematic diagrams illustrating that the core member 45 comprises a first head portion 130 comprising a first outer surface 135, a first neck portion 140 extending from the first head portion 130, and a third hole 145 in the first neck portion 140. In an example, the first head portion 130 may be diametrically larger than the first neck portion 140. The diameter of the first head portion 130 may be slightly smaller than the diameter of the groove 175 on the second side 170 of the first plate 15 in order for the first head portion 130 to fit in the groove 175. The diameter of the first neck portion 140 may be slightly smaller than the diameter of the first hole 60 of the first body portion 55 of the first plate 15 and the second hole 70 of the second body portion 65 of the second plate 30 in order for the first neck portion 140 to fit in the first hole 60 and the second hole 70. Additionally, the diameter of the first neck portion 140 may be slightly smaller than the diameter formed by the inner annular configuration of the aligned first set of outwardly projecting members 25 with the second set of outwardly extending projecting members 40 in order for the first neck portion 140 to fit in the annular portion of the aligned first set of outwardly projecting members 25 with the second set of outwardly extending projecting members 40. Moreover, the height of the first neck portion 140 may be larger than the spacing 235 between the first plate 15 and the second plate 30 when the device 10 is assembled. The height/thickness of the first head portion 130 is configured to fit and rest in the groove 175 on the second side 170 of the first plate 15 such that the first outer surface 135 of the first head portion 130 is substantially flush with the surface 250 of the first plate 15 when the device 10 is assembled and the core member 45 is positioned in the first hole 60 of the first body portion 55 of the first plate 15 and the second hole 70 of the second body portion 65 of the second plate 30. Additionally, the height of the first neck portion 140 may be greater than the height/thickness of the first head portion 130. According to some examples, the first neck portion 140 may be substantially smooth or may be threaded. In the example where the first neck portion 140 is threaded, the corresponding first hole 60 and second hole 70 may have complementary threads to engage the threads of the first neck portion 140. The third hole 145 may be configured to extend partially through the first neck portion 140 of the core member 45.

FIGS. 7A through 7D, with reference to FIGS. 1A through 6D, are schematic diagrams illustrating that the connecting member 50 comprises a second head portion 150 comprising a second outer surface 155, and a second neck portion 160 extending from the second head portion 150. In an example, the second head portion 150 may be diametrically larger than the second neck portion 160. The diameter of the second head portion 150 may be slightly smaller than the diameter of the groove 195 on the second side 190 of the second plate 30 in order for the second head portion 150 to fit in the groove 195. The diameter of the second neck portion 160 may be smaller than the diameter of the second hole 70 of the second body portion 65 of the second plate 30 and slightly smaller than the diameter of the third hole 145 of the core member 45 in order for the second neck portion 160 to fit in the first hole 60 and the second hole 70. The height/thickness of the second head portion 150 is configured to fit and rest in the groove 195 on the second side 190 of the second plate 30 such that the second outer surface 155 of the second head portion 150 is substantially flush with the surface 260 of the second plate 30 when the device 10 is assembled and the core member 45 is positioned in the first hole 60 of the first body portion 55 of the first plate 15 and the second hole 70 of the second body portion 65 of the second plate 30, and the connecting member 50 is connected to the core member 45.

As such, the first head portion 130 extends through the first hole 60 of the first body portion 55 of the first plate 15 and in the second hole 70 of the second body portion 65 of the second plate 30, and the second neck portion 160 engages the third hole 145 of the core member 45. The engagement of the second neck portion 160 with the third hole 145 of the core member 45 may occur by press fit, threaded/screw, or any other suitable engagement. In the example where the second neck portion 160 is threaded, the corresponding third hole 145 may have complementary threads to engage the threads of the second neck portion 160. Additionally, the height of the second neck portion 160 may be greater than the height/thickness of the second head portion 150. Moreover, the height of the second neck portion 160 may be slightly smaller than the height of the third hole 145, according to an example.

Figure 8:
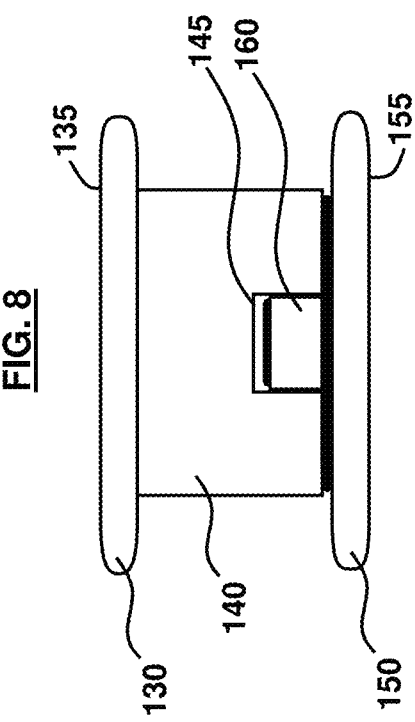
FIG. 8 is a schematic diagram illustrating a cross-sectional side view of the connection of the core member with the connecting member of the intervertebral implant device of FIGS. 1A and 1B, according to an embodiment herein.

FIG. 8, with reference to FIGS. 1 through 7D, is a schematic diagram illustrating that the first outer surface 135 of the first head portion 130 and the second outer surface 155 of the second head portion 150 face in opposite directions from each other. In the view of FIG. 8, the first plate 15 and the second plate 30 along with the corresponding first set of outwardly projecting members 25 and the second set of outwardly projecting members 40 are not shown so as to not obscure the view of the connection between the core member 45 and the connecting member 50. In an example, the diameter of the first head portion 130 may be substantially the same as the diameter of the second head portion 150. As such the groove 175 of the first plate 15 and the groove 195 of the second plate 30 may be configured to be substantially the same as each other, according to an example.

Figure 9:
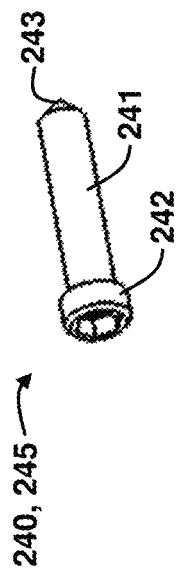
FIG. 9 is a schematic diagram illustrating a perspective view of the first or second fixation member of the intervertebral implant device of FIGS. 1A and 1B, according to an embodiment herein.

FIG. 9, with reference to FIGS. 1A through 8, is a schematic diagram illustrating the at least one first fixation member 240 or the at least one second fixation member 245. In this regard, the at least one first fixation member 240 and the at least one second fixation member 245 may be configured to be substantially similar to each other. The fixation members 240, 245 each comprise an elongated shaft portion 241 extending from a head portion 242. The diameter of the head portion 242 is larger than the diameter of the elongated shaft portion 241. Moreover, the diameter of the elongated shaft portion 241 may be slightly smaller than the respective diameters of the first at least one hole 80 of the first fixation component 20 and the at least one hole 100 of the second fixation component 35. The height/length of the elongated shaft portion 241 may be greater than the height/length of the head portion 242. Additionally, the at least one hole 80, 100 may each terminate with a lip (not shown) configured in the first bar 205 of the first fixation component 20 and the second bar 220 of the second fixation component 35 to act as a stop for the head portion 242 when the at least one first fixation member 240 and the at least one second fixation member 245 are inserted into the at least one hole 80, 100, which retains the head portion 242 in the first bar 205 and the second bar 220 without slipping out/through. Furthermore, in some examples, the elongated shaft portion 241 may be anti-rotational and may be substantially smooth or may be threaded, partially threaded, or have spikes (not shown) extending therefrom, or a combination thereof, and may have a pointed end 243, which may allow the elongated shaft portion 241 to dig and set into vertebral bone. In the example where the elongated shaft portion 241 is threaded or partially threaded, the corresponding at least one hole 80, 100 may have complementary threads to engage the threads of the elongated shaft portion 241. According to some examples, the head portion 242 may be configured to accommodate any suitable type of driving mechanism or tool such as a screwdriver, Allen wrenches, and other similar driving mechanisms or tools to allow the at least one first fixation member 240 and the at least one second fixation member 245 to be driven into the vertebral body and set therein.

As shown in FIGS. 1A through 9, the intervertebral implant device 10 comprises the first plate 15 comprising a first surface 250, and a second surface 255 opposed to the first surface 250. The second surface 255 comprises the first set of projecting members 25 outwardly extending from the second surface 255. The device 10 also includes the second plate 30 comprising a third surface 260, and a fourth surface 265 opposed to the third surface 260. The fourth surface 265 comprises the second set of projecting members 40 outwardly extending from the fourth surface 265. The second set of projecting members 40 are configured to complimentarily align adjacent with the first set of projecting members 25. The device 10 also includes the core member 45 that extends through the first plate 15 and the second plate 30. In an example, the core member 45 limits movement of the first plate 15 away from, or in relation to, the second plate 30. The device 10 also includes the connecting member 50 that connects to the core member 45. Moreover, the device 10 also includes the at least one first fixation member 240 that is configured to engage the first fixation component 20 of the first plate 15. Furthermore, the device 10 also includes the at least one second fixation member 245 that is configured to engage the second fixation component 35 of the second plate 30.

Figure 10:
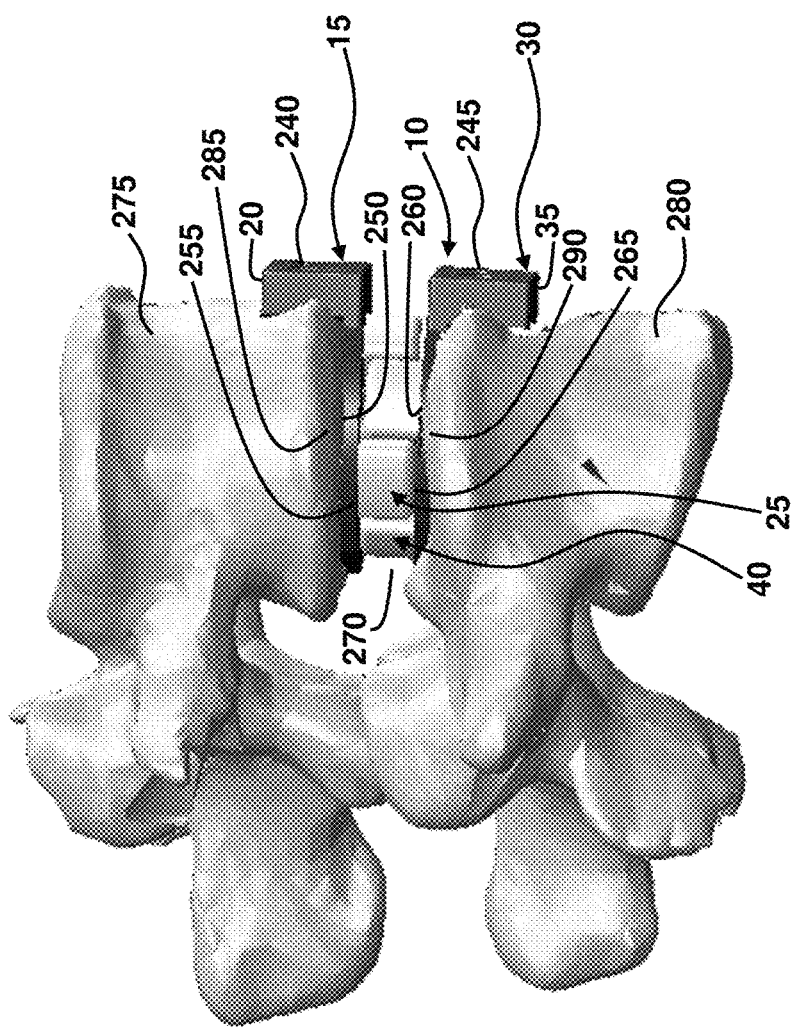
FIG. 10 is a schematic diagram illustrating a perspective view of the intervertebral implant device of FIGS. 1A and 1B implanted into an intervertebral space, according to an embodiment herein.

FIG. 10, with reference to FIGS. 1A through 9, is a schematic diagram illustrating an intervertebral implant device 10 for insertion into an intervertebral space 270 between a first vertebra 275 and a second vertebra 280. The device 10 shown in FIG. 10 is shown in a neutral position; i.e., without compression, flexion, or rotation of the first vertebra 275 and/or the second vertebra 280. The device 10 comprises the first plate 15 comprising the first surface 250 that contacts a first end plate 285 of the first vertebra 275. The device 10 also comprises the second surface 255 opposed to the first surface 250. The second surface 255 comprises the first set of outwardly extending projecting members 25 that are flexible and compressible. The device 10 also includes the second plate 30 comprising a third surface 260 that contacts a second end plate 290 of the second vertebra 280. The device 10 further comprises a fourth surface 265 opposed to the third surface 260. The fourth surface 265 faces the second surface 255. Moreover, the fourth surface 265 comprises the second set of outwardly extending projecting members 40 that are flexible and compressible. The first fixation component 20 is attached to the first plate 15. The first fixation component 20 accommodates the at least one first fixation member 240 that operatively connects the first plate 15 to the first vertebra 275. Moreover, the second fixation component 35 is attached to the second plate 30. The second fixation component 35 accommodates the at least one second fixation member 245 that operatively connects the second plate 30 to the second vertebra 280.

Figure 11:
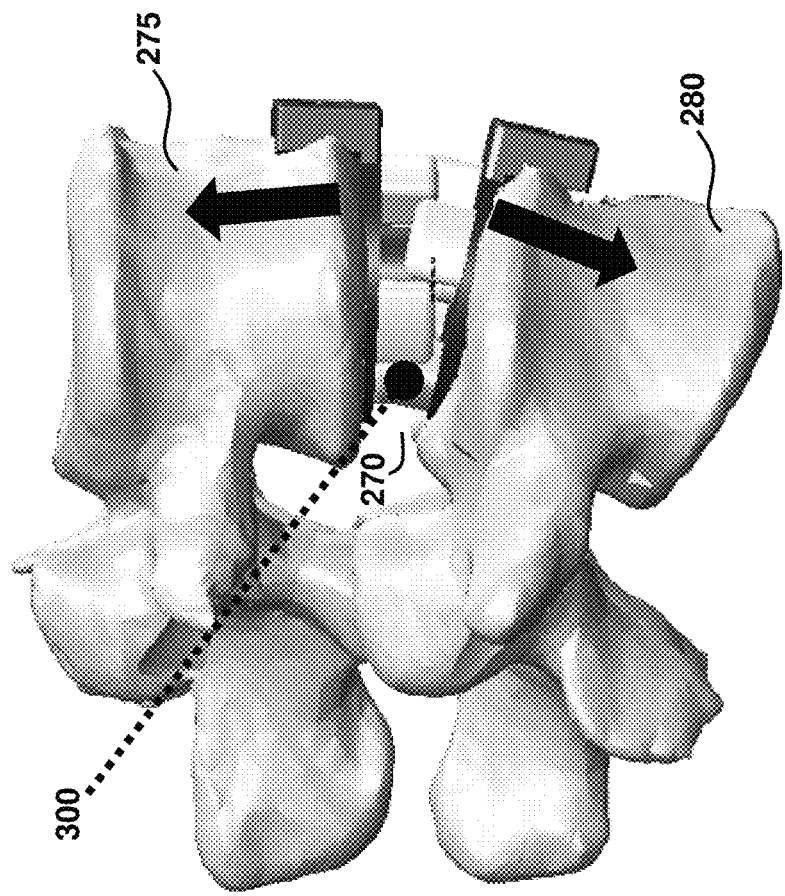
FIG. 11 is a schematic diagram illustrating a perspective view of the intervertebral implant device of FIGS. 1A and 1B implanted into an intervertebral space with vertebrae in a state of extension, according to an embodiment herein.
Figure 12:
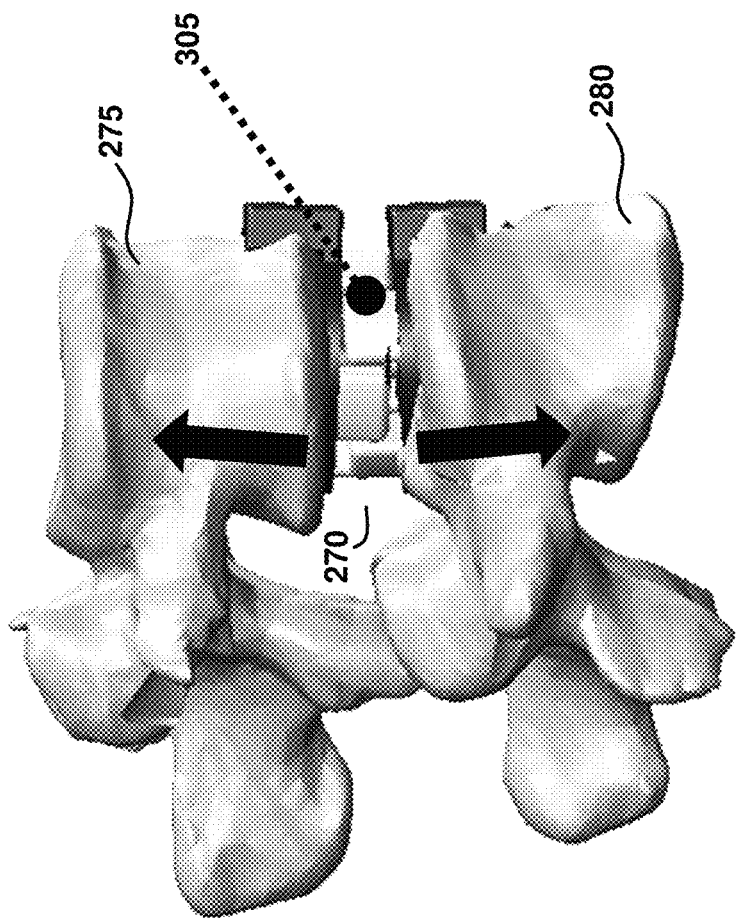
FIG. 12 is a schematic diagram illustrating a perspective view of the intervertebral implant device of FIGS. 1A and 1B implanted into an intervertebral space with vertebrae in a state of flexion, according to an embodiment herein.

FIG. 11, with reference to FIGS. 1A through 10, illustrates a state of extension of the intervertebral space 270 as denoted by the arrows indicating opposite forces of the respective first vertebra 275 and the second vertebra 280. The location of the center of rotation 300 in the state of extension is denoted by the enlarged dot in FIG. 11. Moreover, FIG. 12, with reference to FIGS. 1A through 11, illustrates a state of flexion of the intervertebral space 270 as denoted by the arrows indicating opposite forces of the respective first vertebra 275 and the second vertebra 280. The location of the center of rotation 305 in the state of flexion is denoted by the enlarged dot in FIG. 12. The flexibility of the first set of outwardly extending projecting members 25 and the second set of outwardly extending projecting members 40 allow for a shifting center of rotation for extension/flexion and lateral flexion of the first vertebra 275 and the second vertebra 280. As shown in FIGS. 11 and 12, with extension or flexion, the first set of outwardly extending projecting members 25 and the second set of outwardly extending projecting members 40 may shift with respect to each other. However, the first set of outwardly extending projecting members 25 remain confined within the second plurality of spaces 127, and the second set of outwardly extending projecting members 40 remain confined within the first plurality of spaces 120. Furthermore, the connection of the core member 45 with the connecting member 50 ensures that the first plate 15 and the second plate 30 does not exceed the height of the spacing 235, which helps the device 10 to retain its assembled state upon implantation and helps limit the extension of the intervertebral space 270.

FIGS. 13A through 13C, with reference to FIGS. 1A through 12, illustrate a neutral position, clockwise rotation, and counterclockwise rotation, respectively, of the intervertebral implant device 10. As indicated in FIG. 13A, the second set of projecting members 40 complimentarily align between the first set of projecting members 25 creating an annulus 295 between the first plate 15 and the second plate 30. The device 10 also includes the core member 45 that extends through the first plate 15 and the second plate 30. The core member 45 extends through the annulus 295 and limits an extension of the intervertebral space 270. The connecting member 50 is configured to connect to the core member 45 and is further configured to retain operative connectivity of the first plate 15 with the second plate 30.

FIGS. 13A through 13C illustrate the view shown of the intervertebral implant device 10 below the first plate 15. Thus, the second plate 30 is shown in these views as well as the showing the location of the connecting member 50 as connected with the core member 45, while the first plate 15 is not shown in these views. Moreover, the first plurality of annulus sector members 115 are shown to fit into the second plurality of spaces 127 and adjacent to the second plurality of annulus sector members 125. Furthermore, the second plurality of annulus sector members 125 are shown to fit into the first plurality of spaces 120 and adjacent to the first plurality of annulus sector members 115. Upon rotation of the first vertebra 275 and the second vertebra 280, the intervertebral implant device 10 undergoes rotation. Accordingly, upon rotation (either clockwise as in FIG. 13B or counterclockwise as in FIG. 13C), the first plurality of annulus sector members 115 compress against adjacent second plurality of annulus sector members 125 creating gaps 310. The gaps 310 generally correspond to the locations of the first plurality of spaces 120 and the second plurality of spaces 127. However, the gaps 310 may not be as large or wide as the first plurality of spaces 120 or the second plurality of spaces 127. The flexibility of the first set of outwardly extending projecting members 25 and the second set of outwardly extending projecting members 40 control the rotation of the device 10 such that while the flexibility permits some rotational movement to accommodate some natural rotation of vertebral bodies (i.e., the first vertebra 275 and the second vertebra 280), the annulus 295 retains a sufficiently rigid configuration to permit excessive rotation of the device 10 once implanted in the intervertebral space 270. In this regard, the annulus 295 formed by the aligned first set of outwardly extending projecting members 25 and the second set of outwardly extending projecting members 40 comprise a compressible material that creates an unbreakable, yet accommodating, nucleus and that adapts to the changes in the center of rotation of vertebral bodies (i.e., the first vertebra 275 and the second vertebra 280) due to the ability of the first set of outwardly extending projecting members 25 and the second set of outwardly extending projecting members 40 to retain rigidity after applying a selected amount of force thereon, and the connecting between the core member 45 and the connecting member 50 helps to limit the extension of the intervertebral space 270.

Figure 14:
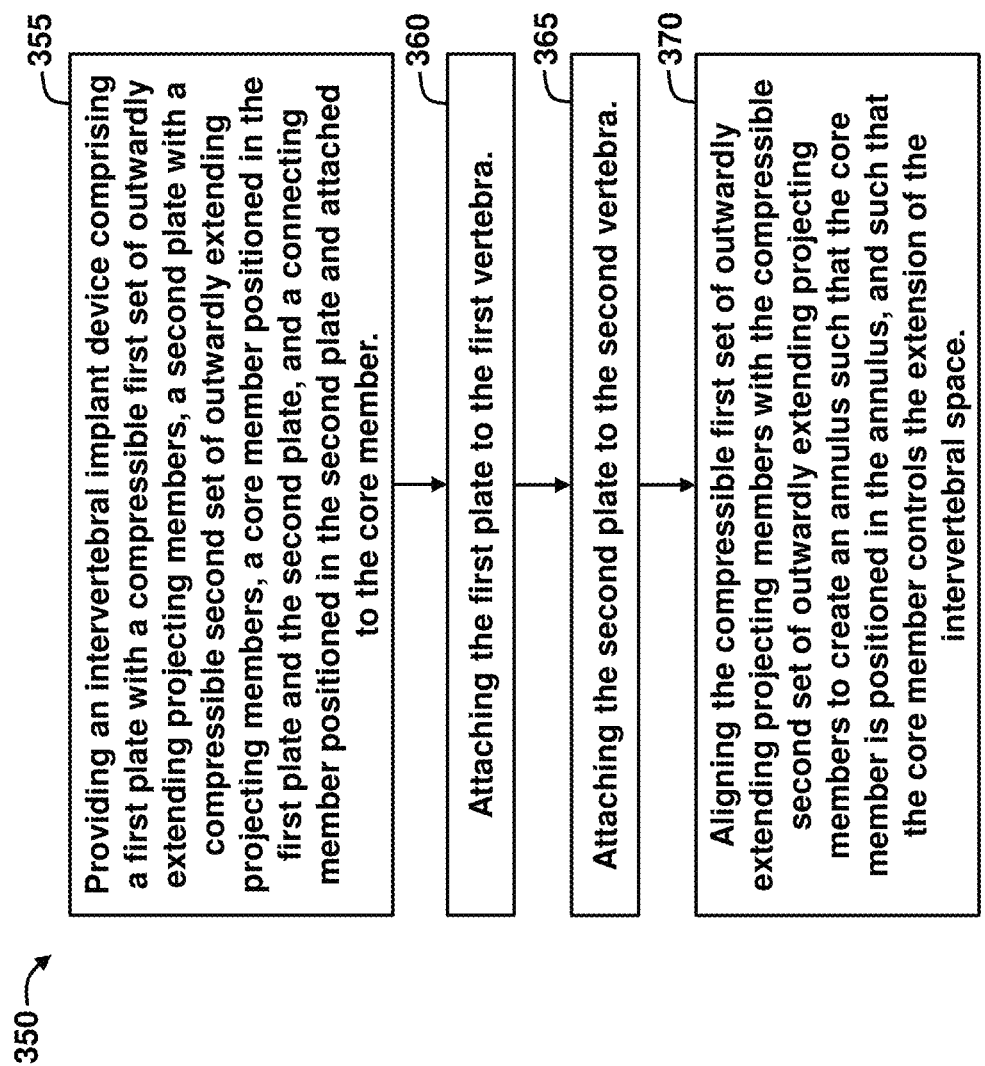
FIG. 14 is a flow diagram illustrating a method of inserting the intervertebral implant device of FIGS. 1A and 1B into an intervertebral space, according to an embodiment herein.

FIG. 14, with reference to FIGS. 1A through 13C, is a flow diagram illustrating a method 350 of inserting an intervertebral implant device 10 into an intervertebral space 270 between a first vertebra 275 and a second vertebra 280. The method 350 comprises providing (355) an intervertebral implant device 10 comprising a first plate 15 with a compressible first set of outwardly extending projecting members 25, a second plate 30 with a compressible second set of outwardly extending projecting members 40, a core member 45 positioned in the first plate 15 and the second plate 30, and a connecting member 40 positioned in the second plate 30 and attached to the core member 45. The method 350 also comprises attaching (360) the first plate 15 to the first vertebra 275. The method 350 further comprises attaching (365) the second plate 30 to the second vertebra 280. Additionally, the method 350 comprises aligning (370) the compressible first set of outwardly extending projecting members 25 with the compressible second set of outwardly extending projecting members 40 to create an annulus 295 such that the core member 45 is positioned in the annulus 295, and such that the core member 45 controls the extension of the intervertebral space 270. According to an example, the alignment of the compressible first set of outwardly extending projecting members 25 with the compressible second set of outwardly extending projecting members 40 may occur automatically upon assembly of the intervertebral implant device 10 and attachment of the first plate 15 and the second plate 30 to the first vertebra 275 and second vertebra 280, respectively.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:
1. An intervertebral implant device comprising:
   a first plate comprising:
      a first fixation component; and
      a first set of outwardly extending projecting members;
   a second plate comprising:
      a second fixation component; and
      a second set of outwardly extending projecting members that align with the first set of outwardly extending projecting members;
   a core member that extends through the first plate and the second plate, wherein the core member limits movement of the first plate away from the second plate; and
   a connecting member that connects to the core member,
   wherein the first plate comprises a first body portion comprising a first hole configured therethrough, wherein the first hole accommodates the core member, wherein the second plate comprises a second body portion comprising a second hole configured therethrough, wherein the second hole aligns with the first hole, and wherein the second hole accommodates the core member and the connecting member,
   wherein the core member comprises:
      a first head portion comprising a first outer surface;
      a first neck portion extending from the first head portion; and
      a third hole in the first neck portion,
   wherein the connecting member comprises:

a second head portion comprising a second outer surface; and a second neck portion extending from the second head portion, wherein the first head portion extends through the first hole of the first body portion of the first plate and in the second hole of the second body portion of the second plate, and wherein the second neck portion engages the third hole of the core member.

2. The device of claim 1, wherein the first fixation component extends from an outer edge of the first body portion of the first plate, wherein the first fixation component comprises a first at least one hole configured therethrough, and wherein a first axis through the first hole of the first body portion and a second axis through the first at least one hole of the first fixation component are perpendicular to each other.

3. The device of claim 2, wherein the second fixation component extends from an outer edge of the second body portion of the second plate, wherein the second fixation component comprises a second at least one hole configured therethrough, and wherein a third axis through the second hole of the second body portion and a fourth axis through the second at least one hole of the second fixation component are perpendicular to each other.

4. The device of claim 3, wherein the first axis and the third axis are co-linear.

5. The device of claim 3, wherein the second axis and the fourth axis are parallel.

6. The device of claim 1, wherein the first set of outwardly extending projecting members comprise a first plurality of annulus sector members spaced apart from each other by a first plurality of spaces, and wherein the first plurality of annulus sector members are positioned in a substantially annular arrangement on the first plate.

7. The device of claim 6, wherein the second set of outwardly extending projecting members comprise a second plurality of annulus sector members spaced apart from each other by a second plurality of spaces, and wherein the second plurality of annulus sector members are positioned in a substantially annular arrangement on the second plate.

8. The device of claim 7, wherein the first plurality of annulus sector members fit into the second plurality of spaces and adjacent to the second plurality of annulus sector members, and wherein the second plurality of annulus sector members fit into the first plurality of spaces and adjacent to the first plurality of annulus sector members.

9. The device of claim 1, wherein the first outer surface of the first head portion and the second outer surface of the second head portion face in opposite directions from each other.

10. The device of claim 1, wherein the first body portion of the first plate comprises a first side and an oppositely facing second side, wherein the first side comprises the first set of outwardly extending projecting members, wherein the second side comprises a groove and a plurality of outwardly extending spikes, and wherein the groove accommodates the first head portion of the core member.

11. The device of claim 1, wherein the second body portion of the second plate comprises a first side and an oppositely facing second side, wherein the first side comprises the second set of outwardly extending projecting members, wherein the second side comprises a groove and a plurality of outwardly extending spikes, and wherein the groove accommodates the second head portion of the connecting member.

12. The device of claim 2, wherein the first fixation component comprises a first bar containing the first at least one hole, wherein the first bar comprises a first side and an oppositely positioned second side, wherein the second side is adjacent to the first plate, and wherein the second side is substantially arcuately shaped.

13. The device of claim 3, wherein the second fixation component comprises a second bar containing the second at least one hole, wherein the second bar comprises a first side and an oppositely positioned second side, wherein the second side is adjacent to the second plate, and wherein the second side is substantially arcuately shaped.

14. The device of claim 1, wherein a spacing between the first plate and the second plate is defined by a height of any of the first set of outwardly extending projecting members and the second set of outwardly extending projecting members.

15. The device of claim 3, comprising:
at least one first fixation member that engages the first at least one hole of the first fixation component; and
at least one second fixation member that engages the second at least one hole of the second fixation component.

16. The device of claim 3, wherein the first body portion, the second body portion, the first fixation component, and the second fixation component are formed of a first material that is substantially rigid, and wherein the first set of outwardly extending projecting members and the second set of outwardly extending projecting members are formed of a second material that is substantially flexible.

17. An intervertebral implant device comprising:
a first plate comprising:
a first surface; and
a second surface opposed to the first surface, wherein the second surface comprises a first set of projecting members outwardly extending from the second surface;
a second plate comprising:
a third surface; and
a fourth surface opposed to the third surface, wherein the fourth surface comprises a second set of projecting members outwardly extending from the fourth surface, wherein the second set of projecting members are configured to complimentarily align adjacent with the first set of projecting members;
a core member that extends through the first plate and the second plate, wherein the core member limits movement of the first plate away from the second plate;
a connecting member that connects to the core member;
at least one first fixation member configured to engage the first plate; and
at least one second fixation member configured to engage the second plate,
wherein the first plate comprises a first body portion comprising a first hole configured therethrough, wherein the first hole accommodates the core member, wherein the second plate comprises a second body portion comprising a second hole configured therethrough, wherein the second hole aligns with the first hole, and wherein the second hole accommodates the core member and the connecting member,
wherein the core member comprises:
a first head portion comprising a first outer surface;
a first neck portion extending from the first head portion; and
a third hole in the first neck portion,
wherein the connecting member comprises:

a second head portion comprising a second outer surface; and a second neck portion extending from the second head portion, wherein the first head portion extends through the first hole of the first body portion of the first plate and in the second hole of the second body portion of the second plate, and wherein the second neck portion engages the third hole of the core member.

18. An intervertebral implant device for insertion into an intervertebral space between a first vertebra and a second vertebra, the device comprising:
a first plate comprising:
  a first surface that contacts a first end plate of the first vertebra; and
  a second surface opposed to the first surface, wherein the second surface comprises a first set of outwardly extending projecting members that are flexible;
a second plate comprising:
  a third surface that contacts a second end plate of the second vertebra; and
  a fourth surface opposed to the third surface, wherein the fourth surface faces the second surface, wherein the fourth surface comprises a second set of outwardly extending projecting members that are flexible, and wherein the second set of projecting members complimentarily align between the first set of projecting members creating an annulus between the first plate and the second plate;
a core member that extends through the first plate and the second plate, wherein the core member extends through the annulus and limits an extension of the intervertebral space;
a connecting member that connects to the core member and retains operative connectivity of the first plate with the second plate;
a first fixation component attached to the first plate, wherein the first fixation component accommodates at least one first fixation member that operatively connects the first plate to the first vertebra; and
a second fixation component attached to the second plate, wherein the second fixation component accommodates at least one second fixation member that operatively connects the second plate to the second vertebra,
wherein the first plate comprises a first body portion comprising a first hole configured therethrough, wherein the first hole accommodates the core member, wherein the second plate comprises a second body portion comprising a second hole configured therethrough, wherein the second hole aligns with the first hole, and wherein the second hole accommodates the core member and the connecting member,
wherein the core member comprises:
  a first head portion comprising a first outer surface;
  a first neck portion extending from the first head portion; and
  a third hole in the first neck portion,
wherein the connecting member comprises:
  a second head portion comprising a second outer surface; and
  a second neck portion extending from the second head portion,
wherein the first head portion extends through the first hole of the first body portion of the first plate and in the second hole of the second body portion of the second plate, and wherein the second neck portion engages the third hole of the core member.

19. The device of claim 17, wherein the first outer surface of the first head portion and the second outer surface of the second head portion face in opposite directions from each other.

20. The device of claim 19, wherein the first outer surface of the first head portion and the second outer surface of the second head portion face in opposite directions from each other.

\* \* \* \* \*

UNITED STATES PATENT AND TRADEMARK OFFICE
CERTIFICATE OF CORRECTION

PATENT NO. : 11,071,632 B2
APPLICATION NO. : 16/840381
DATED : July 27, 2021
INVENTOR(S) : Oh et al.

Page 1 of 1

It is certified that error appears in the above-identified patent and that said Letters Patent is hereby corrected as shown below:

In the Claims

Column 18, Line 35, please delete "19" and insert --18-- in its place.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*